United States Patent [19]

Volke

[11] Patent Number: 4,693,858
[45] Date of Patent: Sep. 15, 1987

[54] METHOD OF PROCESSING HYDROCOLLOID DRESSINGS

[75] Inventor: Robert W. Volke, Garrettsville, Ohio

[73] Assignee: Variseal Manufacturing Corp., Parkman, Ohio

[21] Appl. No.: 855,716

[22] Filed: Apr. 25, 1986

[51] Int. Cl.[4] ............................................. B29C 47/88
[52] U.S. Cl. ................................... 264/101; 264/102; 264/171; 264/176.1; 264/177.17; 264/213; 264/237; 264/288.8; 264/289.3; 264/338; 264/348

[58] Field of Search ............... 264/237, 345, 348, 346, 264/213, 338, 101, 166, 102, 175, 348, 171, 280, 210.2, 176.1, 177.17

[56] References Cited

U.S. PATENT DOCUMENTS

| | | | |
|---|---|---|---|
| 2,232,109 | 2/1941 | Gibbons | 264/175 |
| 2,451,597 | 10/1948 | Wheeler | 264/280 |
| 2,708,289 | 5/1955 | Collings | 264/338 |
| 2,842,800 | 7/1958 | Cochran | 264/344 |
| 2,985,912 | 5/1961 | Johnson | 264/130 |
| 3,972,328 | 8/1976 | Chen | 128/156 |
| 4,226,818 | 10/1980 | Brower et al. | 264/348 |
| 4,379,806 | 4/1983 | Korpman | 264/171 |
| 4,400,338 | 8/1983 | Rundo | 264/171 |
| 4,538,603 | 9/1985 | Pawelchak et al. | 128/156 |
| 4,551,490 | 11/1985 | Doyle et al. | 524/22 |

*Primary Examiner*—Jeffery Thurlow
*Attorney, Agent, or Firm*—Reese Taylor

[57] ABSTRACT

A method of processing hydrocolloid adhesive material includes the steps of extruding a sheet of the hydrocolloid adhesive material from a vacuum extruder, applying a liner of release material to at least one side of the sheet, under pressure, and while the sheet is at an elevated temperature and maintaining the liner and the sheet under tension during cooling of the sheet.

7 Claims, 5 Drawing Figures

METHOD OF PROCESSING HYDROCOLLOID DRESSINGS

RELATED APPLICATIONS

None.

BACKGROUND OF THE INVENTION

This invention relates in general to the handling and processing of pressure-sensitive adhesive compositions and relates in particular to the processing of a pressure-sensitive adhesive composition for ultimate use as a component of hydrocolloid dressings intended to be applied to the skin of human beings.

DESCRIPTION OF THE PRIOR ART

In the art of wound care, it is often necessary to apply dressings for varying lengths of time to wounds, both elective and traumatic. Such dressings are intended to keep out contamination and absorb excess exudate. In certain situations, therefore, it is desirable to apply an absorbent dressing pad which, generally, takes the form of an outer film layer and an inner adhesive-absorbent layer comprising a composite formulation of a hydroactive colloid with an elastomer and with this dressing layer being self-adhering to the skin surface. In order to achieve this adherency, pressure-sensitive adhesives of various types have been developed for use in the formulation of the adhesive-absorbent or hydrocolloid layer.

To achieve the desired degree of adherence to the skin, it is necessary to develop certain tack characteristics in such adhesive.

It is also desirable to integrate ingredients that do not lend themselves to smooth extrusions into the adhesive-absorbent layer to inhibit cold flow during storage and/or application to the patient and maintain structural integrity as the layer picks up moisture during use. On a laboratory basis, of course, such adhesives can be developed and in a rudimentary process, dressings of this type can be provided as a laminate of a film layer, an adhesive-absorbent layer and a release layer.

However, when transferring this technology to a production environment wherein large quantities are to be produced on a more or less continuous basis, serious problems are encountered in handling the adhesive and processing it, due, to a large degree, to its inherent tackiness and surface topography. Thus, the very features which make the adhesive-absorbent component of the dressing desirable in use, make it difficult to process.

SUMMARY OF THE INVENTION

It is accordingly an object of this invention to provide a process and method for producing hydrocolloid dressings with suitable pressure-sensitive adhesives as a part of the dressing and on a continuous basis.

A further object of the invention is to provide such a system capable of satisfactorily handling such a dressing where the adhesive component contains ingredients to increase the absorbency and stability of the dressing in use.

It is a further object of this invention to provide such a process, wherein the ingredients can be employed in the product while still producing an end product having a smooth surface and capable of absorbing large degrees of moisture. In that regard, it is an object of this process to introduce the adhesive component to the dressing with a minimal amount of moisture present therein, so as to make the end product capable of absorbing greater amounts of moisture in use.

These objects are accomplished by the utilization of a vacuum extruder, which removes considerable moisture from the product, and a take-up apparatus for applying constant high pressure and tension to pull the liner tight and to apply this pressure so as to pull the ingredients down into the composition, smooth out surface topography and avoid lumpiness during the cooling cycle.

Accordingly, production of an improved manufacturing process of the character above-described becomes the principal object of this invention with other objects thereof becoming more apparent upon the reading of the following brief specification considered and interpreted in view of the accompanying drawings.

OF THE DRAWINGS

BRIEF DESCRIPTION OF THE PREFERRED EMBODIMENT

As previously noted, an object of this invention is to produce, on a continuous basis, the material of a hydrocolloid dressing of the type generally described above. One component of this dressing is a pressure-sensitive adhesive absorbent layer which is capable of adhering to the skin of the patient, and is also capable of assisting in the absorption of moisture at the point of application.

Figure 1:
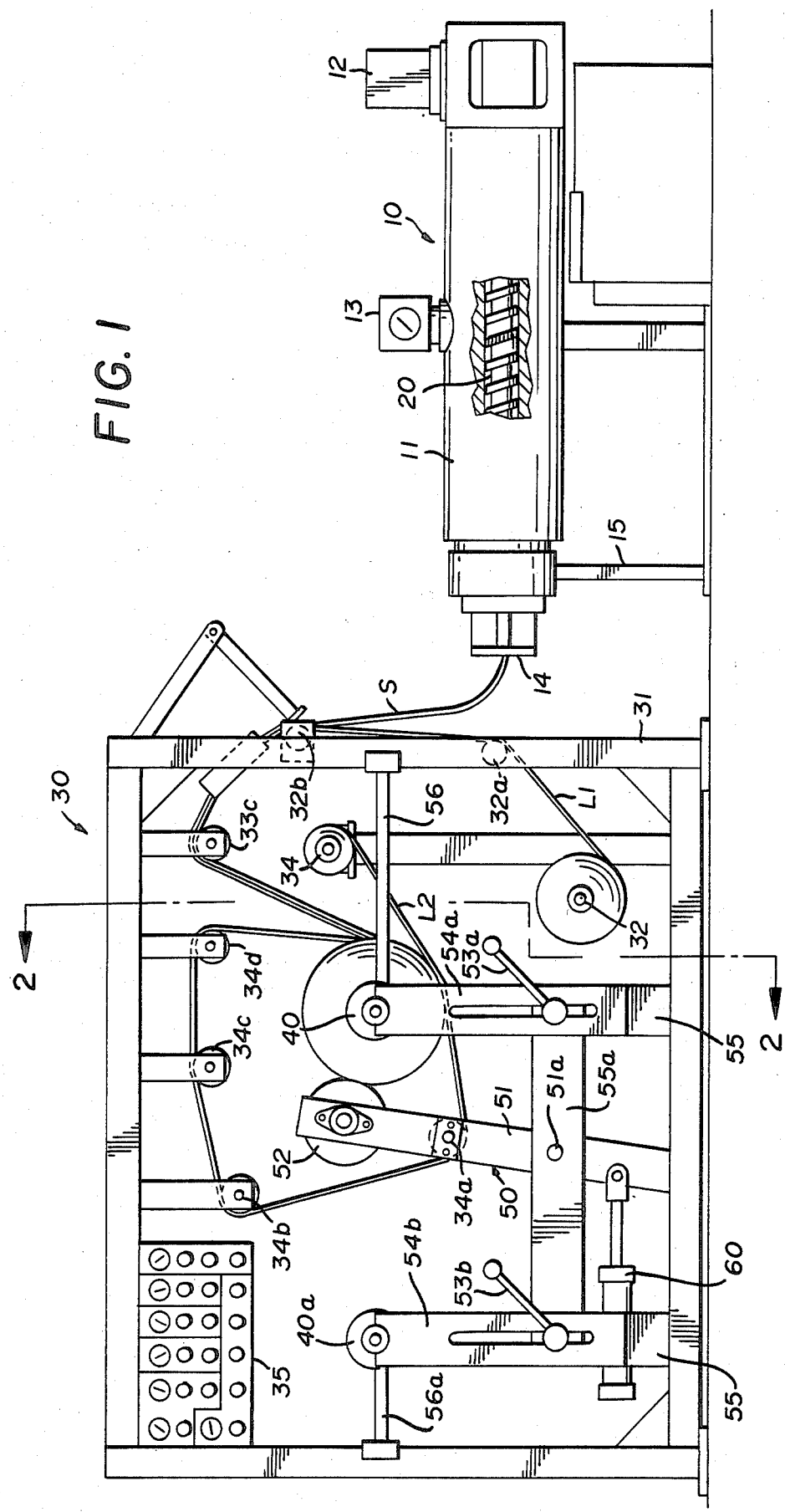
FIG. 1 is an elevational, partially schematic view showing apparatus capable of carrying out the process.
Figure 2:
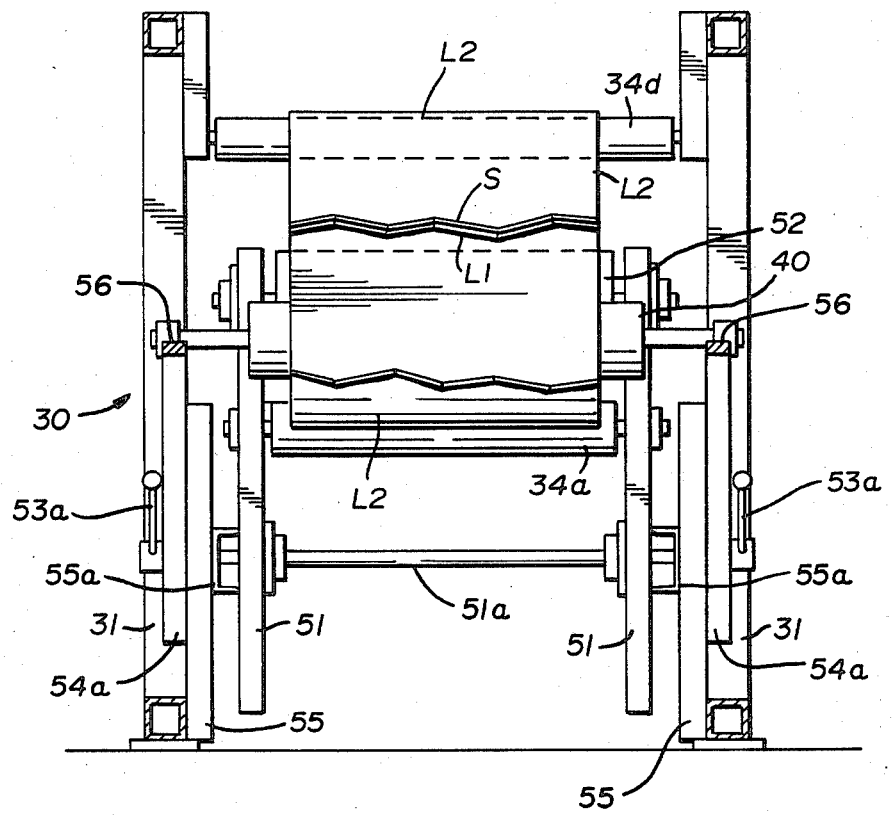
FIG. 2 is a sectional view taken along the line 2—2 of FIG. 1.

Referring then to the drawings for a brief description of the apparatus employed to accomplish the process, it will be noted from FIG. 1 that a rather conventional extruding apparatus, generally indicated by the numeral 10, is associated with a take-up apparatus, generally indicated by the numeral 30, which takes the form of what is commonly called a center surface winder.

Referring still to FIG. 1, it will be noted that the extrusion apparatus 10 includes an elongate body 11 supported on a frame 15 and having a feed opening 12, wherein the raw material can be fed to the interior of the extruder. Examples of typical material of this nature are disclosed in Doyle U.S. Pat. No. 4,551,490; Pawelchak U.S. Pat. No. 4,538,603 and Chen U.S. Pat. No. 3,972,328.

A vacuum means 13 is mounted approximately at the midpoint of the extruder body 11, and an extrusion die 14 is mounted at the end opposite the feed opening 12.

Received internally of the housing 11, is a feed screw 20 which is capable of melting and conveying the plasticated material.

Figure 3:
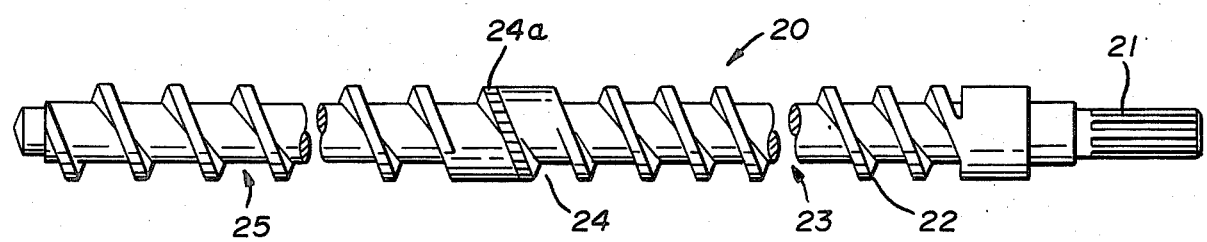
FIG. 3 is an elevational view of the extruder screw.

Referring to FIG. 3 for a brief description of the feed screw 20, it will be noted that this is essentially a vacuum extruder screw of the type fairly well known in the rubber mixing art, and includes a spline end 21 which can be engaged with a suitable drive means so as to rotate the screw relatively of the body 11.

The screw also includes at least one continuous helical flight 22 and, includes the usual feed, mixing and metering sections 23, 24 and 25. The mixing section 24 is associated with the vacuum means 13 so that, as the material is fed along the helical flight 22, the material, when it passes through the mixing area 24 and particularly through the grooves 24a of that area, is subjected to a vacuum which extracts a considerable percentage of the existing moisture and trapped air from the composition. The material is then passed along the screw 20 and exits the apparatus through die 14 in a sheet S.

Extrusion apparatus of this general type is fairly conventional in related arts and is not described here in great detail, since construction of such apparatus would be well known to one of ordinary skill in this art.

Turning then to the wind-up or take-up apparatus 30, it will be noted that the same includes a framework 31 upon which are supported various components.

A film supply roll 32 is thus rotationally mounted thereon, and serves as a supply source for the film $L_1$. This film constitutes a release member such as silicone coated paper and is threaded from the supply roll 32 over the rolls 32a, 32b and 32c toward the wind-up roll 40 as shown in FIG. 1.

The adhesive-absorbent material S leaves the extrusion apparatus 10 through the die 14 as previously noted, and meets the film material $L_1$ adjacent the roll 32b passing beneath sensor 60 which is a photo-electric loop sensor which synchronizes the take up apparatus with the extruder. These components (S and $L_1$) then form a two-layer sandwich or laminate from that point to the take-up or wind-up roll 40 passing over the roller 33c together.

A second liner or release material $L_2$ is also fed from supply roll 34 beneath the take-up roll 40 and around a series of rollers 34a, 34b, 34c, 34d to the driven take-up or wind-up roll 40. At that point, the liner $L_2$ joins the previous two-layer sandwich to form a three-layer sandwich which is then wound up on to the take-up roll 40. The extruder 10 and the roll 40 are controlled by suitable controls on control panel 35.

It will be understood that, depending on the end use of the material, the second liner $L_2$ could be eliminated and the liner $L_1$ could be coated on both sides. In either event, an important feature of the invention is the take-up of the "sandwich" or laminate under pressure.

To that end, pressure and support means 50 are provided. These means include a secondary frame comprising support legs 55, 55 connected by horizontally disposed bars 55a, 55a. These bars 55a, 55a serve as a support for weighted arms 51, 51 and pressure roll 52 with the arm being pivotally mounted by the shaft 51a.

A hydraulic pump 60 is mounted adjacent the left hand side of FIG. 1 and is connected to the lower end of arm 51 by a suitable piston. In this fashion the arm 51 can be moved about pivot point 51a to increase or decrease pressure on roll 40.

Also, to facilitate removal and replacement of roll 40, slotted legs 54a, 54b are disposed outwardly of support legs 55, 55 and bars 55a, 55a and are connected thereto by locking means 53a and 53b. Thus, to remove roll 40, locking means 53a can be released and slotted leg 54a dropped down to permit the roll 40 to be removed.

It will be noted that since roll 52 applies considerable pressure on roll 40, bar 56 can be employed to resist this force and maintain roll 40 in its proper position. During removal of roll 40, bar 56 can be swung out of the way about its point of attachment to frame 31.

It has been found that by applying constant tension and high pressure on the laminate with structure of this general nature, that the liner will be maintained in a very tight condition and will apply pressure to the adhesive layer S. This has the effect of compressing the rough topography and smoothing it out with it being understood that as the adhesive layer S leaves the extrusion device 10, it is at an elevate temperature so that at this point, by taking it up onto the roll 40 under constant and high pressure, the adhesive absorbent layer will be compressed and ironed and the other surface thereof will remain smooth during the cooling process.

Once the roll 40 is removed from apparatus and a suitable cooling period has taken place, it is possible to strip the laminate off the roll 40 and remove the liner $L_2$ at which time it can be die cut to the desired final configuration.

It should be noted that roll 40 can be changed quickly and easily, as described above, with only extremely brief down time. However, if a more or less continuous operation is desired, roll 40a can be employed. This roll is mounted on slotted leg 54b, which operates similar to leg 54a and also has bar 56a associated with it, as is the case with bar 56.

Of course, arm 51 and roll 52 can be applied in this mode by pivotting it to the opposite hand position from that illustrated in FIG. 1.

In the form of the invention just described, the cooling process occurs at ambient temperature. However, in some situations greater speed may be desired and alternative apparatus may be employed to practice essentially the same process.

Figure 4:
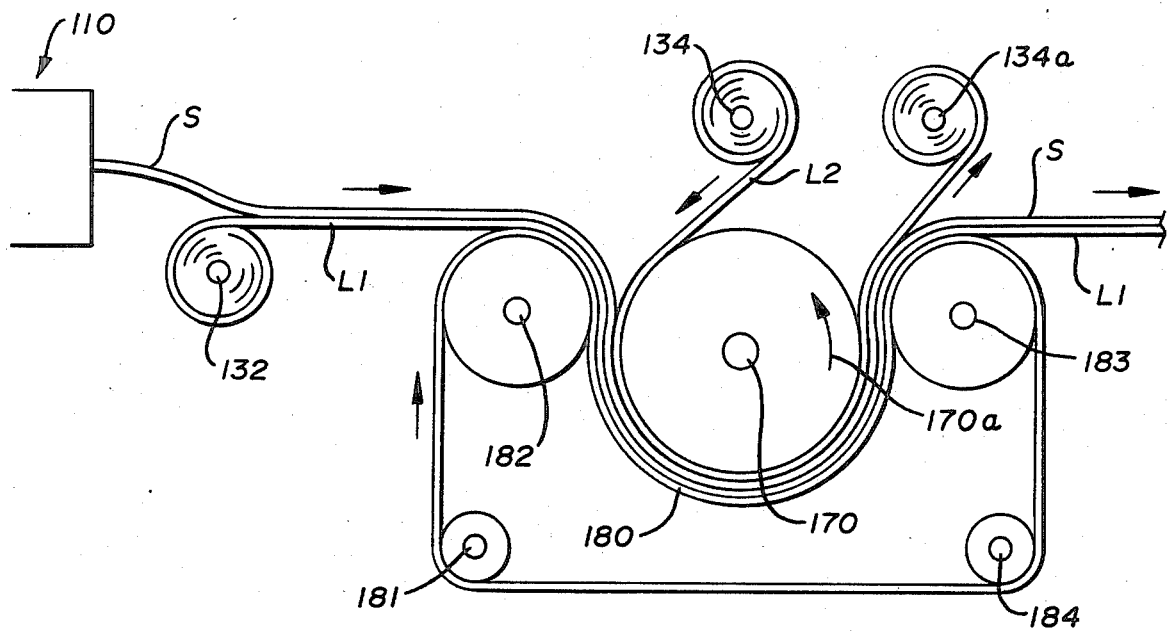
FIG. 4 is a schematic view of alternative apparatus for carrying out the process.

Thus, and referring to FIG. 4 of the drawings, a rotocure apparatus can be employed to shorten the cooling period.

To that end, an extruder 110, similar to the extruder 10 of FIG. 1, provides a sheet of the materials and the first liner $L_1$ is supplied by supply roll 132. A second liner $L_2$ is supplied by roll 134.

A chilled drum 170 is driven in the direction of arrow 170a and the laminate of material S and liners $L_1$ and $L_2$ are passed about its periphery. To provide the desired pressure, an endless flexible belt of a material such as stainless steel is passed about rolls 181, 182, 183 and 184 so as to press the laminate against the periphery of chilled drum 170.

The essential steps of the inventive process are thus duplicated with the apparatus of FIG. 4, but the cooling time is greatly reduced.

It should be noted that FIG. 4 illustrates liner $L_2$ being taken up on roll 134a, but this could be an endless sheet of material if desired.

Figure 5:
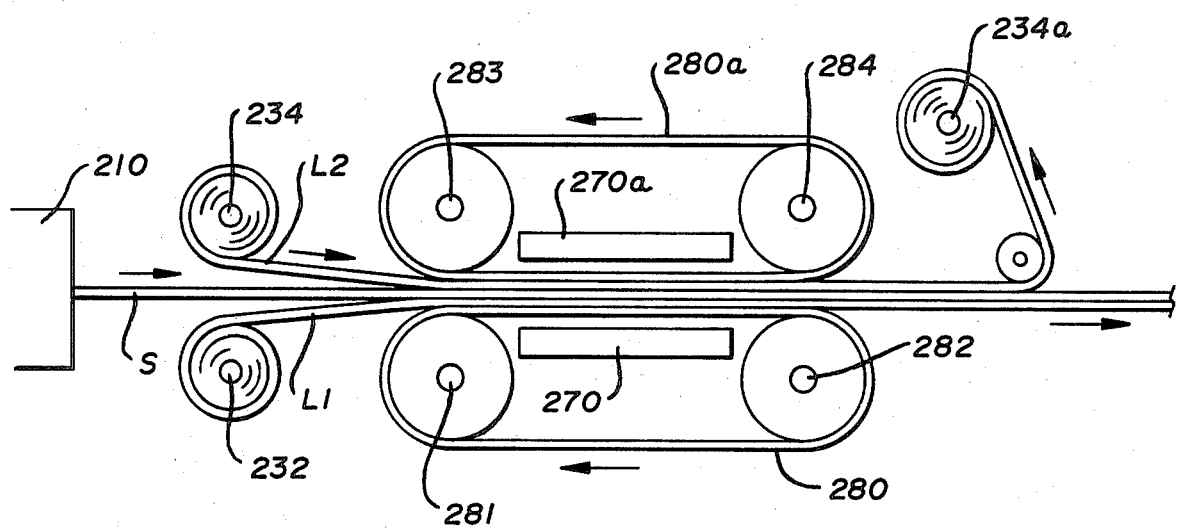
FIG. 5 is a schematic view of a further alternative apparatus for carrying out the process.

FIG. 5 illustrates further modified apparatus for practicing the inventive process.

Thus an extruder 210 is provided to supply the sheet of material S and roll 232 supplies the liner $L_1$ while roll 234 supplies the liner $L_2$.

The laminate thus formed is pressed between conveyor belts 280, 280a which are driven around rolls 281, 282 and 283, 284 to supply the necessary pressure and chilled plates 270 and 270a are located adjacent the conveyor belts to supply the cooling requirements.

Here again liner $L_2$ is illustrated as being taken up on roll 234a but could be endless. In any event, the essential steps of the inventive process are duplicated with the apparatus of FIG. 5.

While a full and complete description of the invention has been set forth in accordance with the dictates of the Patent Statutes, it should be understood that modifications can be resorted to without departing from the spirit of or the scope of the appended claims.

Thus, several alternative apparatus for carrying out the method have been illustrated and described, but these expedients are not intended to be exhaustive.

What is claimed is:

1. A method of processing hydrocolloid adhesive material, comprising the steps of:
   (A) extruding a sheet of the adhesive material having an initial uneven surface topography from a vacuum extruder;
   (B) applying a liner of release material, under constant pressure, to at least one side of said sheet while the adhesive is at an elevated temperature to thus laminate said liner and said sheet under said pressure to compress said sheet and smooth the initial uneven surface topography thereof;
   (C) maintaining said liner and said adhesive sheet under tension during cooling thereof.

2. The method of claim 1, wherein a second liner is applied to the opposed surface of said adhesive sheet.

3. The method of claim 1 or 2, wherein said adhesive sheet and said liner are wound on a center surface winder, under pressure and with said adhesive sheet at an elevated temperature.

4. The method of claim 3, wherein said sheet is cooled at ambient temperature.

5. The method of claim 1 or 2, wherein said adhesive sheet and said liner are passed about a cooling drum.

6. The method of claim 1 or 2, wherein said adhesive sheet and said liner are passed between opposed cooling plates.

7. The method of claim 1 or 2, wherein said adhesive sheet and said liner are cooled by the application of external cooling means.

* * * * *